US008287908B2

(12) United States Patent
Kristensen et al.

(10) Patent No.: US 8,287,908 B2
(45) Date of Patent: Oct. 16, 2012

(54) PREPARATION OF MOLECULAR IMPRINTED POLYMERS

(75) Inventors: Jesper S. Kristensen, Virum (DK); Klaus G. Nielsen, Søborg (DK); Nicholas O. Krogh, Virum (DK)

(73) Assignee: Mipsalus ApS, Virum (DK)

( * ) Notice: Subject to any disclaimer, the term of this patent is extended or adjusted under 35 U.S.C. 154(b) by 1008 days.

(21) Appl. No.: 12/279,238

(22) PCT Filed: Feb. 21, 2007

(86) PCT No.: PCT/DK2007/000083
§ 371 (c)(1), (2), (4) Date: Aug. 13, 2008

(87) PCT Pub. No.: WO2007/095949
PCT Pub. Date: Aug. 30, 2007

(65) Prior Publication Data

US 2009/0104277 A1 Apr. 23, 2009

Related U.S. Application Data

(60) Provisional application No. 60/743,330, filed on Feb. 21, 2006.

(30) Foreign Application Priority Data

Feb. 21, 2006 (DK) ................................ 2006 00248

(51) Int. Cl.
*C08F 2/38* (2006.01)

(52) U.S. Cl. ....................................................... 424/489

(58) Field of Classification Search ........................ None
See application file for complete search history.

(56) References Cited

U.S. PATENT DOCUMENTS 5,786,428 A * 7/1998 Arnold et al. .............. 525/333.3
5,821,311 A * 10/1998 Mosbach et al. .............. 526/201
5,861,319 A * 1/1999 Lin et al. ....................... 436/527
5,872,198 A * 2/1999 Mosbach et al. .............. 526/201
5,959,050 A * 9/1999 Mosbach et al. .............. 526/201
5,994,110 A 11/1999 Mosbach et al.
6,217,901 B1 4/2001 Perrott et al.
6,379,599 B1 * 4/2002 Vaidya et al. ................. 264/220
6,680,210 B2 * 1/2004 Huang .......................... 436/518
6,852,818 B1 * 2/2005 Piletsky et al. ............ 526/303.1
6,881,804 B1 * 4/2005 Sellergren et al. ......... 526/219.6
2002/0015690 A1 2/2002 Green et al.

FOREIGN PATENT DOCUMENTS

JP 03147025 5/2003
WO 9411403 A1 5/1994
WO 0041723 A1 7/2000
WO 0130856 A1 5/2001
WO 02059184 A2 8/2002
WO 02068958 A1 9/2002
WO 02084292 A1 10/2002
WO 03101580 A1 12/2003

OTHER PUBLICATIONS

Vivek Babu Kandimalla Æ Hunagxian Ju. Molecular imprinting: a dynamic technique for diverse applications in analytical chemistry. Anal Bioanal Chem (2004) 380: 587-605.*

Günter E. M. Tovar, Iris Kräuter, Carmen Gruber. Molecularly Imprinted Polymer Nanospheres as Fully Synthetic Affinity Receptors. Top Curr Chem (2003) 227:125-144.*

E. Turiel • A. Martin-Esteban. Molecularly imprinted polymers: towards highly selective stationary phases in liquid chromatography and capillary electrophoresis. Anal Bioanal Chem (2004) 378:1876-1886.*

Ching-Chiang Hwang, Wen-Chien Lee. C hromatographic characteristics of cholesterol-imprinted polymers prepared by covalent and non-covalent imprinting methods. Journal of Chromatography A, 962 (2002) 69-78.*

Lars I. Andersson. Molecular imprinting for drug bioanalysis A review on the application of imprinted polymers to solid-phase extraction and binding assay. Journal of Chromatography B, 739 (2000) 163-173.*

Gianluca Ciardelli, Cristiana Borrelli, Davide Silvestri, Caterina Cristallini, Niccoletta Barbani, Paolo Giusti. Supported imprinted nanospheres for the selective recognition of cholesterol. Biosensors and Bioelectronics 21 (2006) 2329-2338.*

Paolo Truffa-Bachi and Leon Wofsy. Specific Separation of Cells on Affinity Columns. vol. 66, No. 3, pp. 685-692, Jul. 1970.*

Tan Y., et al.; "A study of a new TSM bio-mimetic sensor using a molecularly imprinted polymer coating and its application for the determination of nicotine in human serum and urine"; Bioelectrochemistry 53, 2001, 141-148.

Dickey FH, "The preparation of specific absorbents"; Proc. Natl. Acad. Sci. 35 (1949) 227-229.

Ramström O et al; "Chiral recognition in adrenergic receptor binding mimics prepared by molecular imprinting"; J. Mol. Recog. 9(1996)691-696.

Schweitz L et al; "Capillary electrochromatography with molecular imprint-based selectivity for enantiomer separation of local anaesthetics"; J Chromatog. A 792(1997)401-409.

(Continued)

*Primary Examiner* — Robert A Wax
*Assistant Examiner* — Olga V Tcherkasskaya
(74) *Attorney, Agent, or Firm* — Harness, Dickey & Pierce, PLC

(57) ABSTRACT

One aspect is a method for improved preparation of molecular imprinted polymer (MIP) particles, where initial compositions comprising insoluble MIP particles are enriched for those MIP particles that bind a particular target molecule, thus excluding non-binding and weakly binding particles from the final composition. Enrichment is typically accomplished via use of chromatographic methods capable of separating particulate material or by means of agglutination. Another aspect is preparation of improved insoluble MIPs by use of extended micronization of raw MIP particles with a view to expose a large number of binding sites per mass unit of MIP particles. In preferred embodiments the two aspects are combined. The resulting improved MIPs may be used for diagnostic, analytical and therapeutic purposes, notably as orally administered drugs which can bind substances such as cholesterol and bile acids and bile acid salts in the gastrointestinal tract.

34 Claims, 3 Drawing Sheets

OTHER PUBLICATIONS

Figure 1:
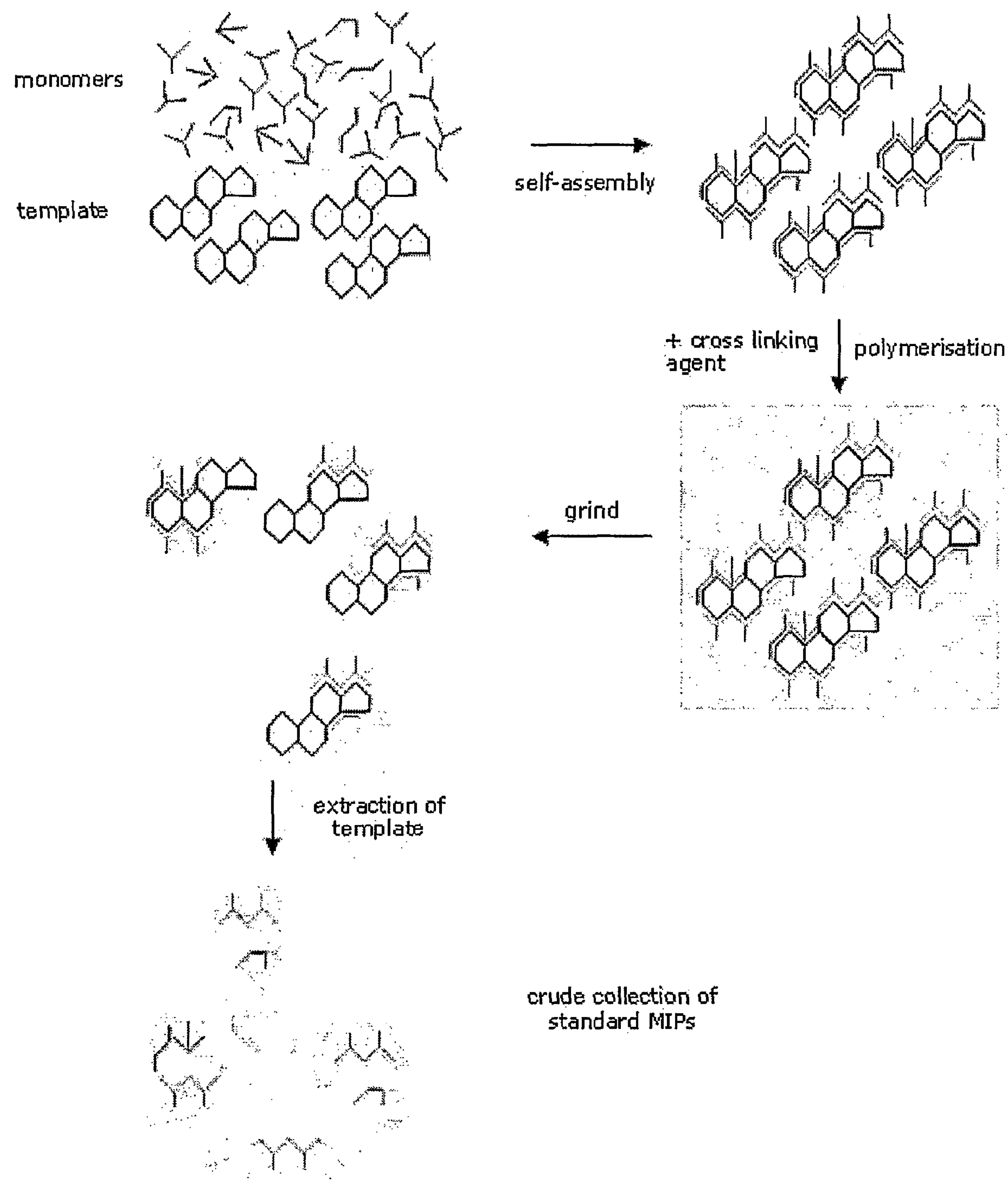

Vlatakis G et al; "Drug Assay Using Antibody Mimics Made by Molecular Imprinting"; Nature 361(1993)645-647.

Funke, W. et al; Microgels—intramolecularly crosslinked macromolecules with a globular structure; Adv. Polym. Sci. 136(1998) 139-243.

Ujam et al; "Insolation of monocytes from human peripheral blood using immuno-affinity expanded-bed adsorption"; Biotechnol Bioeng 83(2003)554-66.

Chase H.A.; "The use of affinity adsorbents in expanded bed adsorption"; J. Mol. Recognit 11(1998)217-221.

Pla et al.; "Evaluation of the energy of red blood cell agglutination by monoclonal antibodies"; Biochem. Biophys. Res. Commun. 277(2000)381-5.

Rodgers et al.; "The development of a semi-automated latex agglutination test for the detection of antibodies to anaplasma marginale using a cell culture-derived antigen"; Ann. NY. Acad. Sci. 849(1998)282-92.

Hansen CM, Hansen Solubility Parameters, A Users Handbook CRC Press (ISBN 0-8493-1525-5.

Shea KJ and Dogherty TK, J. Am. Chem. Soc. 108(1986)1091-1093.

Shea KJ, Stoddard GJ, Shavelle DM, Wakui F and Choate RM Macromolecules 23(1990)4497-4507.

Wulff G and Poll HG Makromol. Chem. 188(1987)741-748.

Sellergren, B. et al. (1998), Chem. Mater. 10; 4037-46.

Pharmaceutical Preformulation and Formulation: A Practical Guide from Candidate Drug Selection to Commercial Dosage Form, Mark Gibson, CRC press, 2001.

Kempe and Mosbach (1991), Anal. Lett. 24, 1137-45.

Ramström et al (1994), Tetrahedron: Asymmetri 5, 649-56.

Ramström et al (1996 I), J. Mol. Recogn. 9, 691-6.

Ramström et al (1996 II), Chem. Biol. 3, 471-7.

Liu and Mosbach (1997), Macromol. Rapid. Commun. 18, 609-25.

Liu andMosbach (1998), Macromol. Rapid. Commun. 19, 671-4.

Corresponding Chinese office action dated Dec. 16, 2011.

* cited by examiner

PREPARATION OF MOLECULAR IMPRINTED POLYMERS

CROSS-REFERENCE TO RELATED APPLICATIONS

This application is a National Stage of International Application No. PCT/DK2007/000083, filed Feb. 21, 2007, which claims the benefit of U.S. Provisional Application No. 60/743,330, filed on Feb. 21, 2006.

The entire disclosures of each of the above applications are incorporated herein by reference.

FIELD

The present disclosure relates to improvements in the preparation of molecular imprinted polymers (MIPs) and in particular the present invention relates to methods that increase the binding capacity and specificity of MIPs so as to render feasible their use as capture agents in pharmaceutical preparations, notably those pharmaceutical preparations that bind target molecules in the gastrointestinal tract e.g. cholesterol and bile acids and bile acid salts. Furthermore this improvement of the preparation of MIPs serves as a means of characterisation of the said MIPs.

BACKGROUND

Molecular imprinting of synthetic polymers is a process where functional and cross-linking monomers are copolymerized in the presence of a target molecule, which acts as a molecular template. Before polymerization, the functional monomers either form a complex with the template via non-covalent interactions, or are covalently coupled forming a polymerizable derivative of the template. After polymerization, the functional groups of the monomers are held in position by the highly cross-linked polymeric structure. Subsequent removal of the template by solvent extraction and/or chemical cleavage reveals binding sites that are complementary in size and shape to the target molecule. In this way, a molecular memory is introduced in the polymer (now termed a “molecular imprinted polymer” or “MIP”), which is now capable of rebinding the target with very high specificity.

Originally, MIPs were employed as stationary phases in HPLC, notably for chiral separation. Subsequently, their use has been extended to other analytical techniques such as thin layer chromatography, capillary electrophoresis, solid-phase extraction, and immunoassay type binding assays. The binding sites often have affinities and selectivities approaching those of antibody-antigen systems. These mimics display some clear advantages over real antibodies for sensor technology. Because of their highly cross-linked nature, MIPs are intrinsically stable and robust, facilitating their application in extreme environments, such as in the presence of acids, bases, or metal ions, in organic solvents, or at high temperatures and pressures. Moreover, MIPs are cheap to produce and can be stored in a dry state at room temperature for long periods of time.

Hence, in principle all MIPs are made in the following way: Monomers and target (or template) molecules are mixed, self assembly occurs, cross binder is added and polymerization can be initiated. After polymerization the polymer is broken down into small fractions and the target molecule is extracted. If the MIPs are put into a solution of target molecules these will rebind to the MIPs (cf. also: Yu Cong; Leif Schweitz; and loana Wärnmark-Surugiu).

The general technological steps in preparation of MIPs are illustrated schematically in FIG. 1.

History of MIPs

One of the first examples of MIP preparation was described as early as in 1949 (Dickey) who used a kind of silica (water glass) for selective recognition of dyes. Much later other kinds of self-organizing systems to build up networks wherein it was possible to bind targets/analytes specifically were described (Ramström et al., Schweitz et al., and Vlatakis et al.)

Choice of Monomers and Polymerization

In the 1970s and 1980s (cf. Shea 1986, Shea 1990 and Wulff 1987) the concept of covalently binding the template/target molecule directly to the polymer used for building the scaffold was described. The claim was that the direct binding would lead to a more homogeneous distribution of binding sites throughout the polymer. However, at the same time this leaves the problem of removing the template after the polymerization. In order to remove the template both a micronization of the polymer and a chemical bond breaking is needed.

Preparing MIPs without tethering the template to one of the monomers used during polymerization often results in good MIPs but the experience in literature is that a lot of the binding sites will contain binding sites that tend to bind the template/analyte in less specific parts of the molecule and hence not giving the desired specificity of the resulting MIPs. This is very important for MIPs used for analytical purposes especially if the object is to separate stereoisomeric forms of molecules, whereas this is less important in the case where the main objective is to enhance the total binding capacity of the resulting MIPs.

In certain analytical situations it has been proven that the template has to be of a different identity i.e. instead of using the actual template the produced MIPs are build over template “mimics” in order not to pollute the sample to be analyzed. It is obvious that finding a template mimic that is capable of ensuring a specific binding between the analyte and MIP is a difficult task.

A completely different method of preparing MIPs is by polymerizing the mixture while the monomer, cross binders and template (or template mimics) are kept in particulate format in an emulsion hence leaving the resultant MIP as a particle directly (Funke et al.). The particle size of MIP made with this process will depend on, amongst other things, the monomer concentration and the stirring rate (determining the droplet size in the emulsion). (In order to get particle sizes down to 1 μm one needs to stir the solution at more than 1000 rpm). According to literature the disadvantages with this type of processes are long preparation times and low yields.

In general the prior art often describes the difficulties of preparing reproducible MIPs where both the capacity and the specificity is not compromised (hence lower than desired). To date, the art has not disclosed a reliable and feasible method of preparing MIP compositions with high binding capacity (Sellergren 1998).

Obtaining a Useful Particle Size

When a bulk forming polymerizing process is used to prepare MIPs, the high degree of cross binding calls for a micronization of the polymer to very small particle sizes before the extraction of the template molecules can be accomplished. Methods for micronization are used in very different industrial areas ranging from the cement industry (creating mm size particles) to small ball mills for thick film paste preparation (μm particle size particles) for electrical circuits. Despite the fact that the micronization process is a crucial part of the MIP functionality (both specificity and capacity) the actual method of choice is not described in details in most MIP literature, whereas it is only mentioned that the bulk polymer obtained is grinded and sieved (particle size sorted) before extraction of the template from the MIPs.

Removal of Template

In most literature the removal of the template molecules is not intensively described despite the fact that this process is crucial for the functionality of the resulting MIP. Most often the process is only mentioned as a non-specified washing procedure using one or more specifically named solvents. Especially if the MIP is developed for use in Solid Phase Extraction (SPE), e.g. as a tool for pre-concentration of analytes, even residual amounts of template will disturb the usability of the MIPs. The sorting of MIP from the matrix used for removal of template is often accomplished by filtration or centrifugation.

Known Efforts to Improve MIPs

U.S. Pat. No. 4,111,863 describes "A non-swellable three-dimensional polymer having a component which is a residue of an optically active compound, which residue is chemically removable from said polymer to leave behind in the physical structure of said polymer a void corresponding to the size and shape of said residue of optically active compound, and a particular steric arrangement of functional groups within the void of said polymer corresponding to the chemical structure of said residue of optically active compound . . . " the optically active compound" being the template that the MIP intentionally should be able to bind subsequently.

In U.S. Pat. No. 5,110,833 "A method of producing synthetic enzymes or synthetic antibodies, comprising the orientation of monomers around a print molecule, addition of crosslinkers, polymerizing to a polymer and subsequent removal of the print molecule, thereby creating a cavity in the polymer corresponding to said print molecule" is claimed to increase specificity of the MIP towards the template molecule. In other words, the performance improvement claimed in U.S. Pat. No. 5,110,833 is based on optimizing the contact between the template molecule and monomer units prior to polymerization.

In U.S. Pat. No. 6,881,804, introduction of porosity in the MIP is described as a means to increase to performance of a MIP by increasing the access to the void that is intended to interact with the template.

In U.S. Pat. No. 6,638,498 specifically selected monomers are claimed for generation of bile acid specific MIP's and in US 2004/0157209 A1, it is suggested to immobilize the template molecule on a support material prior to polymerization. All of the suggestions to improve the performance of MIPs deal with the chemical characteristics of the monomers or the architecture of the MIPs, which are all process steps that take place prior or during the preparation of the MIP.

U.S. Pat. No. 5,994,110 discloses MIPs, which are produced in situ to form small polymers/oligomers, which include a structure complementary to a template molecule. The polymers or oligomers form a coating or image around the biomolecule, which coating or image is removed therefrom, and discrete entities are derived therefrom, which may be used, e.g., as therapeutic or prophylactic agents, i.e. drugs. Due to this type of production process, U.S. Pat. No. 5,994,110 does not utilise a micronization step as in conventional MIP particle preparation. U.S. Pat. No. 5,994,110 does suggest separation of MIPs from non-binders, but the methods suggested all rely on the very small size of the MIPs produced e.g., via chromatography but only when the MIPs are soluble entities. It is e.g. specifically indicated that therapeutically active MIPs according to U.S. Pat. No. 5,994,110 are those which exhibit molecular weights in the lower end of the 1-200 kDa range. Further, U.S. Pat. No. 5,994,110 does not disclose any means for separating suspended insoluble MIPs into "good binders" on the one hand and "less effective or non-binders" on the other.

OBJECT OF THE INVENTION

It is an object of the invention to provide improved methods of preparing MIPs so as to provide MIP compositions having a sufficiently high binding capacity so as to allow such compositions to be used in pharmaceutical applications as an alternative to soluble receptors and antibodies. It is also an object to provide MIP compositions having improved properties over prior art MIP compositions.

SUMMARY

In spite of the above-discussed attempts to improve existing technology for preparation of MIPs, there has today not been any successful attempts of preparing MIP compositions which may be used clinically as a feasible alternative to e.g. antibodies and soluble receptors in methods of treatment, where clearance from the body of a particular target molecule is relevant as part of the therapy.

The present inventors ascribe this to the fact that even though individual MIPs may have a very high affinity for a given ligand, a composition of e.g. micronized/grinded MIPs exhibit a large variety of binding affinities towards the ligand, thus rendering the overall binding capacity unsatisfactory and unsuitable for e.g. clinical use—or, phrased in more simple terms, the binding capacity of known MIP compositions for the target ligand is typically too low to render MIPs a feasible alternative to soluble receptors and antibodies in therapy.

The present inventors have also focussed on the fact that there has been little if any research in influence of MIP particle size on the overall binding capacity of a MIP composition.

The present inventors thus teach to further improve the performance of MIPs by sorting MIP particles after their ability to bind to the template or a template analogue, thereby effecting an up-concentration of effectively target binding MIPs. By such a functional sorting or purification process, a fraction of MIP particles that present a void or cavity with suitable binding ability to the selected template or an analogue, can be generated and hence improve the average affinity between the MIP and the template and thereby the binding capacity of the MIP.

Also, the present inventors have realized that the performance of MIP compositions can be improved simply by improving the micronization steps which have been used to date, thus resulting in MIP particles of smaller average size, whereby they exhibit an improved ratio between binding sites and volume.

Hence, in a first aspect the present invention relates to a method of preparing a composition comprising molecular imprinted polymers (MIPs) having high binding capacity and specificity for a target molecule, said method comprising a) obtaining a suspension of insoluble MIPs, which bind the target molecule, and which have been prepared using the target molecule or a mimic thereof as template molecule, b) subjecting the suspended MIPs to an affinity purification procedure, wherein the template molecule or a fragment thereof or a mimic thereof is used as capture agent, c) recovering the MIPs that bind the capture agent in the affinity purification procedure while substantially excluding the capture agent and MIPs that do not bind the capture agent from the recovered product, and d) combining the MIPs recovered and optionally a carrier, vehicle or diluent to obtain said composition.

In a second aspect, the present invention provides for a method of preparing MIPs having high binding capacity for a target molecule, said method comprising subjecting a raw MIP, which comprises template molecules consisting of said target molecule or a mimic thereof, to a first step of micronization so as to obtain a MIP particle size sufficiently small to allow removal of template molecules, removing substantially all template molecules and optionally subjecting the MIPs thus obtained to a second step of micronization, wherein said first and optionally second steps of micronization provides for a MIP average diameter of at most 50 μm.

In a third aspect, the present invention provides for a composition of insoluble MIPs having at least one of the following characteristics:

1) the average MIP diameter is less than 20 μm;

2) the average target binding is at least 1 mass unit of target to 10 mass units of MIP;

3) substantially all MIPs in the composition bind the same target molecule, and optionally the composition does not include all binding sites for the target molecule.

In a $4^{th}$ aspect, the present invention relates to use of a composition of the invention in the preparation of a pharmaceutical preparation for the treatment, prophylaxis or amelioration of cardiovascular disease, hypertension, atherosclerosis, gallstone disease, cholestatic liver disease, hypercholesterolemia, obesity, infections originating from parasites or microorganisms such as bacteria and fungi, or poisoning originating from orally given toxins.

Finally, in a $5^{th}$ aspect, the present invention relates to a method for treating, ameliorating or reducing the risk of a disease selected from the group consisting of cardiovascular disease, hypertension, atherosclerosis, gallstone disease, cholestatic liver disease, hypercholesterolemia, obesity, infections originating from parasites or microorganisms e.g. bacteria and fungi, poisoning originating from orally given toxins, comprising administering an effective amount of a composition of the invention to a subject in need thereof.

DRAWINGS

FIG. 1: Schematic depiction of a simple MIP preparation procedure.

Figure 2:
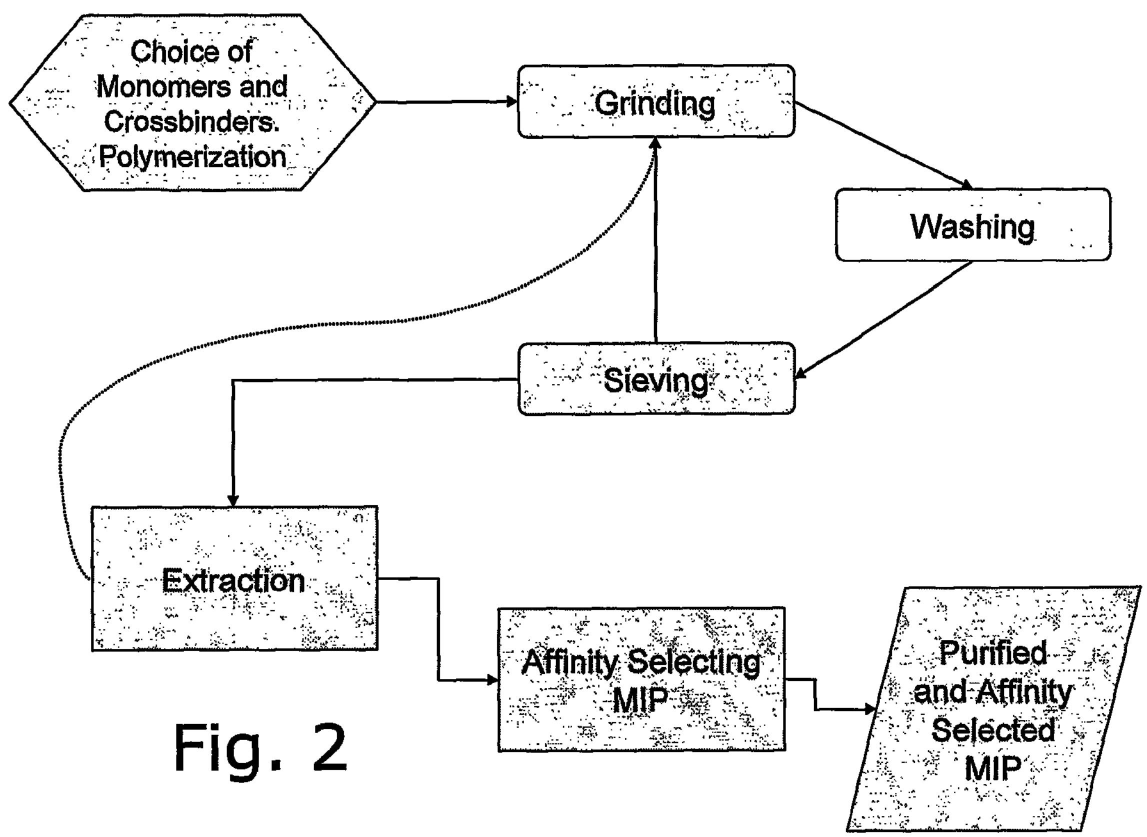
Figure 3:
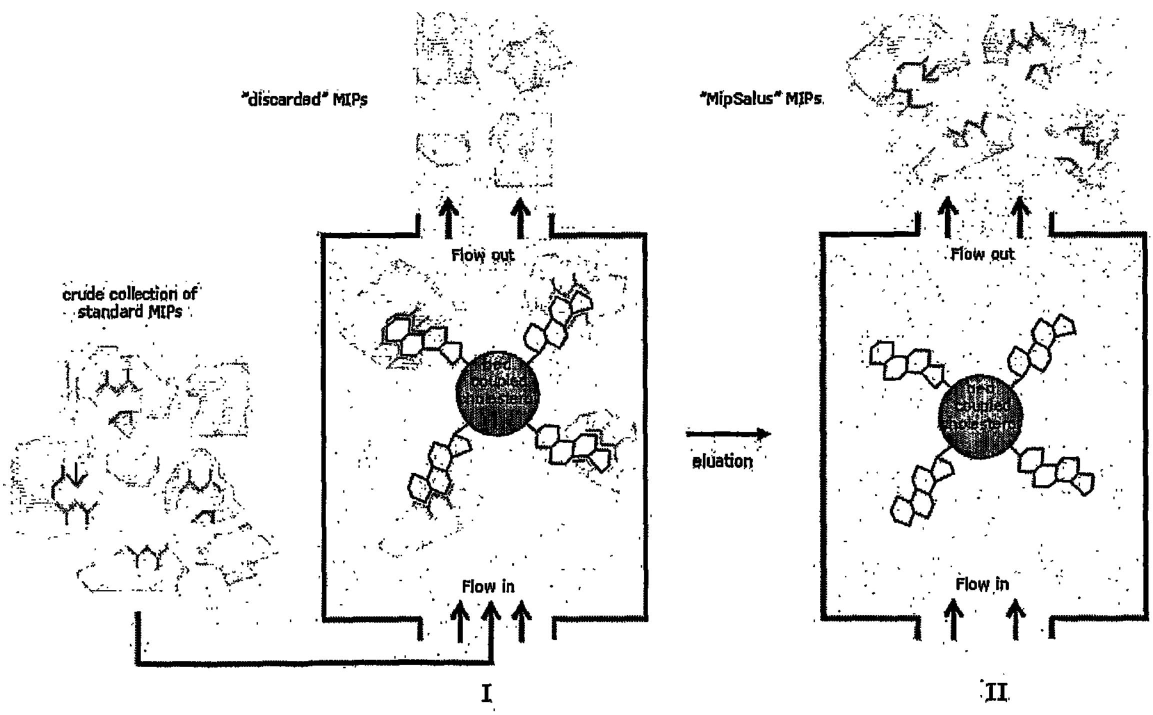

FIG. 2: Simple run through of the inventive processes described herein. The processes can be revisited several times if needed.

FIG. 3, Part I:

Purification or sorting by Expanded Bed Absorption.

MIPs that bind the template, such as a cholesterol like molecule coupled to the bed particle, is retained while the MIPs that do not bind passes through and are discarded.

FIG. 3, Part II

Functionality purified MIPs.

MIPs binding to the template molecule on the bed particle, can subsequently be eluted off. The eluted MIPs will have a higher specific binding capacity than the crude collection of MIPs containing both binding and non-binding MIPs.

Figure 4:
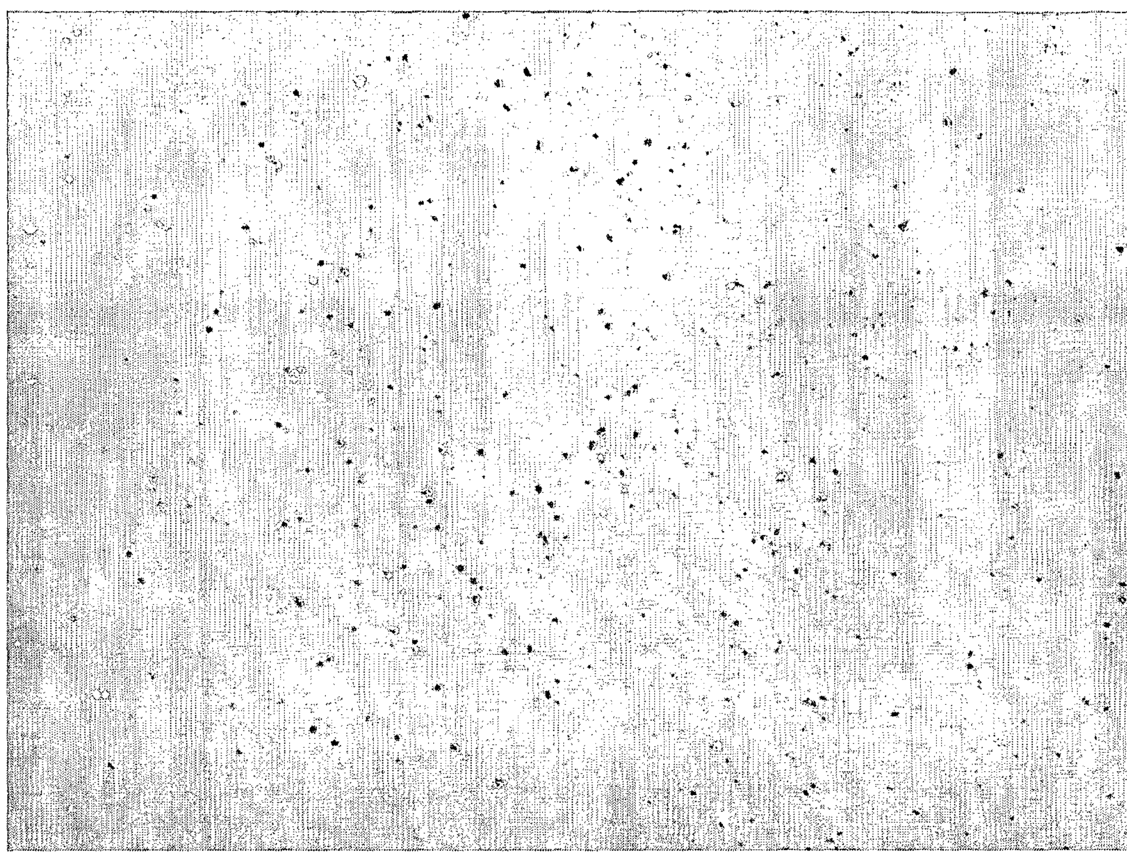

FIG. 4: MIP particles from example 4 in an overlay picture.

The overlay picture is composed of the two pictures taken with visible white light and UV light, respectively. The white spots represent particles illuminated with white light and the black spots represent the UV illuminated green fluorescing particles.

DETAILED DESCRIPTION

Definitions

In the following, a number of terms will be defined in order to ensure a correct understanding of the metes and bounds of the present invention.

A "molecular imprinted polymer" (MIP) is a polymer comprising cavities (or voids) that at least in part correspond to one or more template molecules that have been incorporated in a monomer matrix including cross-linking monomers prior to polymerization. The resulting polymer after polymerization includes a number of cavities which correspond in shape to the template molecule. Typically the MIP is sequestered into small particles, thereby facilitating removal of template and leaving partial cavities open for interaction with a target molecule which resembles or is identical to the template molecule. In the present specification and claims, the term MIP generally refers to the particulate form of a MIP, meaning that the terms "MIP" and "MIPs" are used interchangeably with the expressions MIP particle and MIP particles, respectively.

It will be understood that the MIPs employed in the present invention are insoluble molecules/entities. These MIPs are especially suitable as pharmaceutical for use in the gastrointestinal tract since their insolubility limits or prevents their passage into the body (e.g. into circulation) from the gastrointestinal tract. In other words, when administered orally, the MIPs used in the present invention will substantially remain confined to the gastrointestinal tract until they are disposed off in the feces.

A "raw MIP" is a MIP which has not yet been subjected to any micronization and hence still incorporates template molecules or at least debris derived from template molecules in the cavities in the MIP structure.

"Micronization" denotes the process of sequestering MIPs which may still contain template into smaller particles. Any method suitable for this purpose may be used.

A "target molecule" is in the present context any molecule to which a MIP can bind.

A "template molecule" is normally identical to the target molecule, but may also be a mimic thereof (i.e. a molecule having at least in part an identical 3D structure and profile which matches that of the target molecule—a mimic may for instance be constituted by a fragment of the target molecule). The template serves as the "generator" of the voids in the MIP structure which subsequently are to be able to bind the target molecule.

"Affinity purification" denotes any method for purification of a substance where specific binding between the substance and a binding partner is utilised. Many such methods utilise a capture agent bound to a solid support (such as a chromatographic matrix) which catches the substance. Typical examples known in the art are affinity purification using antibodies as capture agents coupled to chromatographic beads for purifying antigens that bind the antibody. It will be understood that the affinity purification methods applied according to the present invention are those which are capable of capturing suspended insoluble MIP particles having the sizes discussed herein. Hence, a typical affinity purification method could be expanded bed adsorption (EBA) known to a person skilled in the art.

A "solid phase" is in the present context any material which may be used to anchor a capture agent by means of covalent or non-covalent binding. Hence, any material (plastic polymers, sugars, metals, glass, silica, rubber etc) which is conventionally used in the preparation of chromatographic materials may serve as the solid phase. The solid phase material may contain suitable functional groups which allow coupling of the capture agent to the material in question. Such derivatized materials are known to the person of skill in the art of chromatographic purification of proteins and other macromolecules. Further, the solid phase may have any physical form which allows for capture of relatively large and insoluble particles such as MIPs (when comparing with single biomolecules such as proteins). Hence, the solid phase may be in the form of fibers (preferably hollow), a chromatography matrix (preferably a matrix suitable for EBA), beads (preferably those that may be separated by electromagnetic means) or any other suitable form, cf. below.

Embodiments of the Purification Aspect According to the Invention

As specified above, the present invention in its first aspect relates to a method of preparing a composition comprising molecular imprinted polymers (MIPs) having high binding capacity and specificity for a target molecule, said method comprising a) obtaining a suspension of insoluble MIPs, which bind the target molecule, and which have been prepared using the target molecule or a mimic thereof as template molecule, b) subjecting the suspended MIPs to an affinity purification procedure, wherein the template molecule or a fragment thereof or a mimic thereof is used as capture agent, c) recovering the MIPs that bind the capture agent in the affinity purification procedure while substantially excluding the capture agent and MIPs that do not bind the capture agent from the recovered product, and d) combining the MIPs recovered and optionally a carrier, vehicle or diluent to obtain said composition (such carriers, vehicle and diluents are typically selected amongst those that are pharmaceutically acceptable and known to the person skilled in preparation of pharmaceutical compositions comprising solid small-size particles).

In other words, this aspect relies on up-concentration of MIPs that exhibit a desired, sufficiently high affinity for the target molecule (or a surrogate thereof such as a relevant fragment of the target molecule), but this aspect also has the effect that non-binding fragments of an original raw MIP are removed from the MIP composition—in its own right, this increases the binding capacity per mass unit of the MIP particle composition to a significant degree, cf. Example 4 and accompanying FIG. 4. It is believed that the present inventors are the first to demonstrate that state of the art compositions of insoluble MIPs prepared by methods known in the art include a large fraction of non-binding particles, and that the binding capacity per mass unit of any such composition can be improved dramatically by removing the non-binders. It will therefore be understood that any preparation of insoluble MIPs may be subjected to the purification step b), so the 1$^{st}$ aspect of the invention may be combined with any known method for preparing insoluble MIPs, notably those known methods which involve means for obtaining high capacity and/or high specificity MIP compositions.

In the following, various embodiments of purification schemes designed for MIP compositions will be discussed in detail.

A first group of purification schemes comprises that the capture agent is coupled covalently or non-covalently to a solid phase (such as a chromatographic matrix)—i.e. this group of purification schemes i.a. includes typical chromatographic purification methods. Hence, any material useful in chromatography and similar methods is useful, but preferred solid phases are matrices of cross bound carbohydrates, synthetic polymers, metal particles, or combinations thereof.

A second and equally important group of purification schemes are those, wherein the capture agent consists of or is part of a soluble chemical entity (allowing e.g. for purification by means of agglutination, cf. below). Preferred embodiments of this encompass those wherein the capture agent is coupled covalently or non-covalently to a moiety selected from a dendrimer, a substituted carbohydrate, and a substituted soluble polymer such as polyvinyl alcohol and polyethyleneglycol in order to expose multiple capture agents per soluble chemical entity.

Irregardless of whether one or the other group of purification schemes is selected, some embodiments of the first aspect of the invention encompass having the capture agent binding to only a fraction of binding sites in the MIPs defined in step a) that are capable of binding the template molecule. Put in more simple terms, this embodiment ensures that only MIPs having a desired binding specificity or binding affinity are retained in the purification process, whereas e.g. those MIPs having non-specific or weak binding sites are excluded in the purification.

One way to exclude non-specific binding sites in the purification process entails using a capture agent in affinity purification, where said capture agent is a fragment of the template molecule. By selecting this approach, it is possible to omit, in the capture agent, parts of the template molecule which are capable of competing with other molecules for the binding to the MIPs. This is especially practical in cases where the target molecule includes putative cross-reacting binding sites which could give rise to MIPs that would bind to irrelevant targets. By way of example: If one for instance would like to prepare a MIP composition which binds luteinizing hormone, it would be relevant to exclude the $\alpha$-subunit of this molecule in the template, because the $\alpha$ subunits of LH, FSH, TSH, and hCG are identical.

An alternative to this approach is to utilise a setup, where the capture agent comprises the template molecule or mimic thereof or fragment thereof bound to a solid surface or moiety, whichever applicable, in a specific orientation so as to substantially avoid exposure to the MIPs of part of the capture agent—hence, by coupling the capture agent to its solid support or moiety, at a selected functionality so that the orientation of the coupled capturing agent becomes substantially the same on all its coupling partners, it is achieved that part of the capture agent will not be accessible for binding to the MIPs and hence MIPs capable of binding to the non-accessible part of the capture agent will be screened out of the overall purification procedure. The product of such a purification method will therefore be a composition of MIP particles, where substantially all MIP particles in the composition bind a particular target, but where at least one binding site of the target is not bound by the MIP particles in the composition.

Alternatively, and in cases where there is no desire or appreciable advantage or need to limit the binding between the capture agent and the MIPs, it is preferred that the purification method of the invention is one, wherein the capture agent comprises the template molecule or mimic thereof or fragment thereof bound to the solid surface or moiety (whichever applicable), in a non-specific orientation so that substantially all parts of the capture agent are exposed to the MIPs.

In the cases where the capture agent is bound to a solid support, the affinity purification procedure may be selected from any type of suitable purification technology which relies on coupling of capture agents to a solid surface. However, it is preferred that the purification procedure is selected from the group consisting of expanded bed adsorption (EBA), paramagnetic bead separation, and hollow fiber purification.

Expanded Bed Adsorption (EBA)

Conventional chromatographic methods using a packed bed in a column can usually not be used to isolate particulate material due to the tendency of the particles to get non-specifically trapped within the static void of the bed.

The main principle in EBA is to keep the chromatographic medium, also termed "the solid phase," fluidized and thereby, as explained, allow particles to pass through the column. The advantages of using the EBA technology has been described as the possibility of purifying soluble material, in most cases a protein or a peptide, from a crude feed-stock or cell culture, without pre-column clearing steps such as filtration and centrifugation before application of the raw material to the column (van Reis & Zapata; Lihme et al.). The idea is that insoluble or particulate material such as cell debris and precipitates is washed away simultaneously with binding of the target molecules to the solid phase of the bed. In this manner, time and expenses for these processes are reduced, thus rendering EBA a valuable technology which is economically recommendable for the purification of a countless number of molecules. However, if the bed is expanded the increased volume of the static void of the bed allows particulate material to pass through and thereby to get in proper contact with the solid phase of the bed and consequently bind if required affinity between the particulate material in question and the solid phase of the bed is achieved. In this case it has also been shown that EBA can be used for selection of cells and other particulate material (Ujam et al.), in which monocytes from peripheral blood was isolated using a biotinylated anti-CD14 antibody mixed with the crude blood cells and subsequently applied an EBA system where the bed particles had been supplied with streptavidin.

The present inventors have concluded that in a similar way those particles prepared by the MIP technology can be sorted or purified by EBA, if the solid phase, or bed particles, of the EBA system expose a chemical structure similar or identical to the template used to make the said MIP. As it may be important that the MIP particles are transported with the flow of the fluid part of the EBA system, while the bed particles are kept at a relative constant expanded volume, bed particles with relatively high density (>2 g/ml) will probably prove superior in order to separate unbound MIP's from bed-bound MIP's in the fluidization process. An example of such high density beads is given in Ujam et al. Also preferred are bed particles that are either non-porous or exhibit limited porosity, cf. Chase infra. The template, such as cholesterol or bile acid, is coupled, preferably with an orientation(s) that ensures maximal exposure of the structurally and chemically characteristics of the template molecule, to the bed particles and the prepared MIPs with a preferred size from 0.2-50 μm (cf. below) is applied to the fluidized bed and after suitable reaction time, preferably with recirculation of the fluid phase including unbound MIPs, unbound MIPs are washed away e.g. by enhancing the flow velocity or simply by applying clean washing buffer to the EBA system and lead the flow trough to waste. The bound MIPs can be released from the bed particles by applying soluble template, by heat, increased ionic strength or by applying a physical stress to the bed. It should also be possible to utilise bed particles that are either non-porous or exhibit limited porosity as previously discussed (cf. Chase).

As an alternative to expanding or fluidize the bed by a flow-through, the bed could be expanded by mechanical stirring, end-over-end mixing, shaking, ultrasound, and other convection/mass transport increasing methods. Separation of MIP particles bound to bed particles could subsequently be done by suitable fluidization of the bed via a flow-through phase. Alternatively, bound and un-bound MIPs could be separated by differences in density, size, shape, optical properties, by centrifugation, sedimentation, filtration, capture or other means that separate after size and/or weight, density, shape, colour, light emission, light scattering, extension coefficient.

So, as described in the prior art of purification, particles can be sorted or purified by means of EBA, and according to the present invention this can advantageously be applied to particles prepared by MIP technology if the solid phase, or bed particles, of the EBA system expose a chemical structure similar to the template used to make the said MIP.

Separation by Binding to Magnetic Particles

Dynal (Invitrogen) and other companies have developed technologies using paramagnetic beads primarily for purification of soluble molecules, typically proteins, peptide or DNA, but isolation of cells and organelles by specific binding e.g. to an antibody immobilized on the paramagnetic bead has also been presented. The larger beads M450 (450 μm) are recommended for isolation of such particulate material as cells. After the paramagnetic beads carrying the capture molecule, normally an antibody specific for a membrane protein on the cell, and the target, e.g. a cell or other particulate material, have been in contact for an appropriate length of time, the paramagnetic particles now having bound the cell via the antibody are fixed by applying a magnetic field to the samples container. Unbound cells can be washed away when the paramagnetic beads are fixed and when the magnetic field is removed the paramagnetic particles will be released. These beads are commercially available, e.g. from Dynal with different kinds of activation such as tosyl, epoxy, carboxy and amine that can be used to couple the antibody or another capture molecule, such as a template molecule from a MIP synthesis.

By coupling templates such as cholesterol or bile acids to such magnetic particle template reactive MIPs will bind to the particle and can be separated from weaker template binding or non binding MIPs by applying a magnetic field in the same way as cells carrying a specific membrane protein can be isolated.

Separation by Agglutination

Agglutination is a phenomenon that occurs if molecules and particles or cells establish multivalent interactions with formation of networks with changed solubility or suspension properties, having as consequence that the networks can be detected e.g. by change in optical properties or microscopically. Agglutination is primarily used for diagnostic purposes in rapid point-of care tests. The soluble element that promotes the cross-linking e.g. between erythrocytes is often di- or multivalent antibodies (Pla et al.), lectins or an antigen specific for the application (Rogers et al.).

Soluble molecules exposing multiple template or template analogue molecules, such as dendrimeric structures supplied with e.g. cholesterol or bile acids, can be applied to a collection of MIPs that are kept fluidized or in suspension by e.g. mechanical stirring, end-over-end mixing, shaking, ultrasound, a fluid phase flow, etc. The template reactive MIPs will interact with the template molecules exposed e.g. on the dendrimer, and preferably form a network, where the template exposing dendrimeric structure will act as cross-linking agent.

Un-linked MIP particles are separated from the MIP particles integrated in the agglutinate or network by the apparent differences in density, size, shape, optical properties, by centrifugation, sedimentation, filtration, flow-cytometry, capture or other means that separates after size and/or weight, density, shape, color, light emission, light scattering, extension coefficient. Subsequently, the template reactive MIP particles are extracted as single particles by applying stress to the agglutinate or network as heat, organic solvent, shaking, or by applying soluble template in excess.

Embodiments Relating to Micronization of MIPs

In a previous attempt from the prior art to prepare a cholesterol specific MIP, the capacity was limited to 17 mg cholesterol pr g MIP, however, an un-imprinted MIP prepared the same way bound 13 mg cholesterol pr. g MIP (Sellergren 1998). Another attempt obtains capacity even lower, less than 1 mg cholesterol pr. g MIP (Whitcombe 1995).

The present inventors see these prior art problems in obtaining satisfactory binding capacities as a consequence of not enriching for effective binders in the MIP particle compositions.

The simplest model for the template binding capacity on a MIP is a pure area consideration. The area occupied by the template (e.g. cholesterol) as a function of the MIP particle surface area can be used as a guide to determine the demands for particles size and binding efficacy (the percentage of MIP surface area covered by single templates).

Theoretical Considerations:

The following calculated example shown in the results below will be with the template cholesterol on a spherical polymer particle. Cholesterol is assumed to have a molecular diameter of 16 Å (1.6 nm).

The area A covered by a Target (cholesterol) can be considered a circle. That area is given by $A_T = \pi \times r_T^2$ ($r_T$ is the molecular radius of the target)

The area of a sphere (the MIP particle) is given by:

$A_{MIP} = \pi \times d_{MIP}^2$ ($d_{MIP}$ is the diameter of the MIP sphere)

In order to evaluate how much MIP (in mass) is needed to bind a sufficient amount of cholesterol the density of the polymer used is needed. The chosen density will also be subject to certain limits.

The binding capacity of the MIP is the mass of target ($m_T$) that can be bound by a given mass of MIP ($m_{MIP}$):

$$\frac{m_T}{m_{MIP}} = \frac{n_T \cdot M_W^T}{V_{Part} \cdot \rho_{MIP}} = \frac{\frac{A_{MIP}}{A_T} \cdot CA \cdot M_w^T}{V_{MIP} \cdot \rho_{MIP}}$$

CA denotes the Covered Area on the MIP surface by the target.

This can be further reduced to:

$$\frac{m_T}{m_{MIP}} = \frac{M_w^T \cdot CA}{N_A \cdot r_T^2 \cdot \pi \cdot r_{MIP} \cdot \rho_{MIP}}$$

which in mathematic terms provides the intuitively expected results:

Smaller target size provides larger capacity

Smaller MIP particle provides larger capacity

Smaller MIP density provides larger capacity

Description of the Surface of a MIP Particle with Reference to the Binding Attributes Between the Individual Particles The theoretical number of template molecules in a MIP particle as a function of size of particle can be calculated, if the assumption is made that the added template molecules, typically 50 mM, are evenly distributed in the total volume prior to polymerisation. The number of template molecules, and thus the number of possible binding sites in a given volume, e.g. a pulverised particle, can be described by a standard distribution with a given standard deviation. Theoretically this will not influence the variation of particles in that the standard deviation between two sites on a particle $s_x$ is given by:

$$s_x^2 = \frac{\sum (\Delta r - \Delta \bar{r})^2}{n-1}$$

where Δr is the actual distance between two sites and $\overline{\Delta r}$ is the given middle distance between two binding sites, determined by the distribution of template molecules in the particle. n represents the number of binding sites on each particle. As both $\Delta r - \overline{\Delta r}$ and n decrease with decreasing particle size, $s_x$ is not altered by micronisation of particles. Only when the particle is minuscule, smaller than $10^{-8}$ m (cf. Table 1), so that there is an average of less than 1 template molecule per particle, will there be a big dissimilarity in the particles. In practice, this dissimilarity will presumably "spread" "upwards" to also include particles bigger than $10^{-8}$ m, but will diminish with increasing particulate size, and in the case of larger particles with many binding sites, become insignificant.

On the other hand, the orientation of the template molecules will give rise to dissimilarity. If the template molecule's longitudinal direction is orientated perpendicularly on the particle, it has in principle only two directions of orientation, in that we assume that it will not give cause to different binding sites, even if the template molecule in the perpendicular position rotates round its own longitudinal axis. However, if the template molecule's longitudinal direction is orientated in parallel with the particle surface, it could give rise to infinitely more differing binding sites when the template molecule rotates about its own longitudinal axis. In other words, the number of degrees of freedom (possible positions which the template molecule can occupy) in this situation are infinite and each new orientation, as a result of rotation about the longitudinal axis, will in principle create a binding site which is dissimilar to all others. All in all, this means that the orientation of the template molecule gives rise to an infinite number of differing binding sites.

These binding sites can be characterised by their binding constant, Kd, to the template molecule. Some orientations will, even though they differ, clearly give occasion to binding sites with the same Kd, but there will also be binding sites of very different Kd, as will become clear from the following.

Results and Evaluation

Table 1 shows:

Calculations of the theoretical number of template molecules in a spherical shell of a thickness of 0.9 nm as function of size of the particle.

Calculation of the Total Number of Binding Sites that Can be Expected to be Found Calculation of the Expected Number of High Affinity Binding Sites The numbers in the two end columns are calculated based on published observations (Kempe and Mosbach 1991, Ramström et al 1994, 1996 I and 1996 II, Liu, Mosbach 1997 and 1998, Andersson et al 1995). The thickness of the spherical shell is selected as a radius of the dynamic volume that a molecule with a length of 1.8 nm, e.g. cholesterol (Davidson and Hayes, 2002), is assumed to have. Typically MIPs contain 20 μmol binding sites per gram MIPs (Kempe and Mosbach 1991, Ramström et al 1994 and 1996 I, Liu and Mosbach 1997 and 1998), but the variation in binding constants (Kd) is very large, from $10^{-3}$ to $10^{-9}$ M, which is in agreement with the above mentioned assumptions; the share of high-affinity binding sites typically represents less than 1% of the total number of binding sites (Ramström et al 1996 II, Andersson et al 1995). For example, Ramström et al 1996 II, who describe MIPs against differing corticosteroids (e.g. molecules which show a structural similarity to cholesterol) that the share of high-affinity binding sites (<$10^{-6}$ M) are respectively 0.075% and 0.28%. In the calculation for Table 1, the number of high-affinity binding sites is assumed to be 0.5%. In the articles referred to here, the particle size is typically 25 μm. This size is relatively easily attained by treatment of the polymer in a manual mortar.

TABLE 1

Description of number of binding sites in a thin spherical shell as function of particle size.

| Particle diameter (m) | Number of template molecules in 0.9 nm spherical shell with 50 nM template | Number of expected binding sites in spherical shell | Number of expected high affinity binding sites in spherical shell |
|---|---|---|---|
| 1.0E−04 | 847,784,740 | 373,025,285 | 1,865,126 |
| 1.0E−05 | 8,476,474 | 3,729,649 | 18,648 |
| 5.0E−06 | 2,118,737 | 932,244 | 4,661 |
| 1.0E−06 | 84627 | 37,236 | 186 |
| 5.0E−07 | 21,119 | 9,292 | 46 |
| 1.0E−07 | 833 | 366 | 2 |
| 1.0E−08 | 7 | 3 | 0 |

In practice, the maximum number of binding sites which can be achieved with a 10 μm particle, is found to be 3.7 million (Table 1). If a 10 μm particle is pulverised to 1 μm particles, each new 1 μm particle will have 37,000 binding sites, that is, 1% of the original 10 μm particle. In principle the binding sites from the 10 μm particle is thus distributed on 100 new 1 μm particles. As there are a great number of possible differing binding sites, there must be variations in the newly produced 1 μm particles, as they each only contain 1% of the 'dissimilar' binding sites which were present on the 10 μm particle. The same result is achieved if only the fraction of binding sites which are high affinity, that is, 0.5% of the total number, are used. However, as the number of binding sites then becomes smaller, the effect (described in section 1) which results in very few binding sites, will presumable further contribute to the dissimilarity between the individual particles.

The limit for when a 'hole' in the particle is defined as a binding site is debatable, but binding sites with Kd greater than $10^{-5}$ M hardly has any relevance in use for therapeutic applications. The monoclonal antibodies, which are approved as pharmaceuticals on the USA market have Kd-values of less than $10^{-7}$ M (Carter 2006).

Distribution of template molecules in the particles (given the associated standard deviation) will furthermore depend on parameters such as the temperature of the mixture during the polymerisation, viscosity, size of template molecule, interaction with solvent and other monomers, but these parameters are not universal in the same manner as the assessment used here to describe position and orientation. Use of these process parameters will in our opinion be of relevance in promoting the dissimilarities between pulverised particles.

In the above discussion, the number of degrees of freedom refers exclusively to the position of the individual template molecule; the number of degrees of freedom which are linked to the orientation of the template molecule presumably reflects directly on the distribution of low and high affinity binding sites. As we plan to produce particle compositions of high specificity and capacity, we will use a suitably high stringency in the separation so that it will primarily be the high affinity binding sites that that are sorted and selected. When the number of relevant, that is, high affinity binding sites reach a size so that this parameter (the number) also contribute decisively to the dissimilarity is hard to say, but a reasonable estimate is probably at about 1 μm.

There are methods of producing very hard particles with channels which are sufficiently wide so that fluid can flow through them, without being limited to diffusion rate, if it is desired to expose more binding sites than is immediate available on the outer surface of the particle. This method is exploited in chromatographic systems (e.g. supplied by Applied Biosystem) known as Poros™ matrices, where it is possible to run a fast flow without this affecting the resolution, because the flow of fluid through the particles is the same as that of the fluid surrounding the particles. In more traditional matrices for chromatography (i.e. not HPLC) the flow is limited to the diffusion speed into the individual matrix particle.

If it is desired to exploit the intestinal tract's peristalsis to increase contact with cholesterol or bile acid binding MIPs, particles with channels could be an advantage. If a gel is used, the 'exchange' of intestinal fluid would possibly be limited to diffusion rate into the gel. MIPs gels, primarily for the purpose of drug release systems (e.g. release of insulin) which act by the gel opening when the glucose binds to a specific site, have been produced. This evidences that it is actually also possible to produce MIPs with a gel structure. (Wizeman and Kofinas 2001, Seong et al 2002).

Practical Implementation of the Micronization Aspect

Hence, and as apparent from the above, the second aspect of the invention entails a method for preparing MIPs having high binding capacity and specificity for a target molecule, said method comprising subjecting a raw MIP (i.e. a polymerized cross-linked MIP where no substantial extraction of template or micronization of MIP structure has yet been performed), which comprises template molecules consisting of said target molecule or a mimic thereof, to a first step of micronization so as to obtain a MIP particle size sufficiently small to allow removal/extraction of template molecules, removing/extractin substantially all template molecules and optionally subjecting the MIPs thus obtained to a second step of micronization, wherein said first and optionally second steps of micronization provides for a MIP average diameter of at most 25 μm. Hence, by utilising this approach, MIPs are obtained which have a superior ratio between volume and exposed binding sites. It is normally sufficient (and simplest) to utilise only the first micronization step, in order to obtain the desired small MIP particle size, because this will allow for removal of template molecules, but situations can be imagined where separation of template from MIPs is facilitated by having two micronization steps separated by a template removal step.

It is preferred that the MIP average diameter after micronization step(s) is less than 20 μm such as less than 15 μm, less than 10 μm, less than 5 μm, less than 1 μm, less than 900 nm, less than 800 nm, less than 700 nm, less than 600 nm, and even less than 500 nm, 400 nm, 300 nm, and 200 nm.

At any rate, it is preferred that the MIPs in a given composition after micronization do not substantially include particles of more than 50 μm in diameter (such as more than 40, 30, 20, 10, or 1 μm in diameter).

The micronization may be obtained by means of any suitable method for minimizing the size of MIPs, i.e. methods such as grinding, milling, explosion, hammering, ball milling, cryo grinding, and collision homogenisation, as well as any combination of such methods.

It will be apparent from the above, that one very important embodiment of the present invention entails a combination of the $1^{st}$ and $2^{nd}$ aspects of the invention, i.e. a first preparation of MIPs which entails the micronization to small MIP particle size according to the invention followed by the affinity purification schemes detailed under the discussion of the first aspect of the invention.

In most cases MIPs have been used for analytical purposes in chromatographic systems or as protein substitutes in sensors. The size of the MIP particle in such applications is normally in the range of from 25 to 100 μm. These MIP sizes are, as detailed above, far too large to obtain the desired binding capacity when aiming for a MIP composition for e.g. oral use, and further these large MIPs cannot be selected/purified by means of the traditional cell purification methods.

In order to obtain suitable capacity, the size of the MIP particle is hence critical. The simplest way of increasing the capacity of a given mass of MIP is, according to the above, by increasing the area to volume ratio i.e. rendering the MIP particles smaller and/or by enhancing the "active" area (the area of the MIP that is capable of binding the desired analyte). The area to volume ratio increases as the reciprocal diameter i.e. half the diameter doubles the area to volume ratio. This means that one can obtain a 64 fold increase in binding capacity by decreasing the particle diameter from 25 μm to 0.4 μm per mass unit of MIP.

TABLE 2

Increase in area to volume ratio as a function of the particle diameter.

| Particle diameter (μm) | Index |
|---|---|
| 25.0 | 1 |
| 12.5 | 2 |
| 6.3 | 4 |
| 3.1 | 8 |
| 1.6 | 16 |
| 0.8 | 32 |
| 0.4 | 64 |
| 0.2 | 128 |

The increase is indexed to the particle diameter of 25 μm.

It is according to the invention contemplated that MIPs with a diameter in the 0.5 μm range can be further optimized with respect to capacity (area binding fraction) by a functional selection/purification in an EBA system using template coupled bed particles, cf. the above discussion of the first aspect of the present invention. Such MIP particles are in the same size range as cells that are known to be isolated by surface characteristics in EBA systems. In order to reach the desired small particle size it is necessary to grind/mill with multiple methods due to the different methods being optimal suited for different size intervals, cf. below.

In order to get from the bulk polymer to the desired particle size there will often be a need for using more than one grinding method. There exists no technology today that is universally capable of milling all polymers from mm size to sub-μm size.

Downsizing by intercalating water swellable materials compatible with the polymer and using a wetting and a freeze method (e.g. Cryo-Grind™ technology) can very efficiently break the polymer to smaller particles of ~200 μm. In order to ease this process, porous structures in the polymer can be made by adding fibres (e.g. cellulose, cellulose acetate) into the polymer.

Using high template concentrations can create small polymer domains that can provide both high binding capacity and also a structurally weak polymer that can be downsized easily.

Further downsizing to sub-μm particles can be made by employing Nano-milling/Grinding (e.g. NETZSCH bead mills), a top down process that can grind particles from 20 μm down to 40 to 200 nm size. (These types of particles are often used in pharmaceutical products).

Downsizing by accelerating the MIPs with the help from an air jet, liquid jet or similar and letting this high velocity stream of MIPs and carrier hit a solid target using the collision force to break down the MIPs into smaller particle sizes would also be a possible way of downsizing the MIPs.

Finally, as shown in the examples use of physical grinding of MIPs, e.g. in a simple mortar, has proven effective for a number of MIPs.

Further Considerations Pertaining to the Invention

Choice of Polymers for MIP

In order to get good adhesion between two substances the wetting tension must be low i.e. no repulsive force must work against the adsorption of the ligand onto the polymer surface. In order to choose the right materials for MIPs, the Hansen Solubility Parameters (HSP) (cf. Hansen CM) will be taken into account when the monomers for a suitable polymer should be chosen.

In the case of cholesterol, the HSP is determined for the compound and by studying tables of polymers it can be found that very hydrophobic polymers will be a good choice for preparing MIPs capable of binding cholesterol. The HSP for cholesterol is (δD, δP, δH, R)=(20.4; 2.8; 9.4; 12.6) and the listing of polymers for MIP that overlaps with the HSP sphere for cholesterol is High density Polyethylene (HDPE)>Poly-Vinyl Chloride (PVC)>Polyacrylonitrile (PAN)>Polypropylene (PP)>Teflon (PTFE)>Polyvinyl acetate (PVAc)>Polystyrene (PS)>PolyButylMethacrylate (PBMA)>Polycarbonate (PC)>Polystyrene-polymetacrylic acid (PS/PMAA-co-polymer)>Polyethylene terephtalate (PETP)>Polyurethane (PUR)>PolyStyrenAcrylonitril (SAN)>Polymethylmetacrylate (PMMA)>Polyamide e.g. Nylon 66>Polyvinydiflurid (PVDF)>Polyvinylalcohol (PVA). Not all of these polymers will be easily polymerized together with a cross binder and the template but the above list is nevertheless a convenient starting point for selection of the monomers and cross binders that will provide the best suited polymer. Also co-polymers, block-polymers and co-block-polymers (etc.) can be made in order to match the HSP for any given target ligand.

Extraction of Template

Removal of template from MIPs must be done after the downsizing process and before the purification step. If cooling during the downsizing process is required, solvents that dissolve the template well will be an excellent choice as cooling medium.

The removal of template can be obtained by the use of solvents and solvent mixtures either alone or in combination with heat, increased or decreased ion strength. One common used method is the soxhlet extraction method where the MIP is washed with freshly distilled solvent (or azeotropes if mixtures are used) in a semi continuous fashion. If the resultant (and cross bound) MIP is thermo stable (and the template molecule is not), a pyrogenic procedure before extraction can be applied to destroy the template and hence render it easier to remove, e.g. by the use of solvents not commonly used to dissolve the template.

General Findings of the Preparation Aspects of the Invention

The present inventors have realised that in order to prepare a MIP with high capacity, a carefully selected combination of MIP preparation, micronization, removal of template and selection of the usable MIPs should be used, with a particular focus on the microniztation and selection technologies.

Hence, if one combines the traditional methods for MIP preparation and purification with selection and purification methods known from the cellular and/or protein work field, superior results are contemplated.

An example could be: From the MIP technology "Selection of monomers", Micronization, extraction and sieving will be combined with a functional purification such as EBA. By sorting the MIP particles according to their ability to bind to a functionalized matrix/surface of the expanded bed, the traditional "up stream" MIP production is complemented with "down stream" selection and purification steps.

The very simplest run through of the combined processes described above can be seen in FIG. 2.

Typical examples of useful target molecules (or template molecules) for the MIP compositions of the invention are those found in the gastrointestinal tract, such as in the human gastrointestinal tract. Especially preferred target molecules are those which are pathology related. Especially preferred target molecules are selected cholesterol or a bile acid or a bile acid salt, but also toxic substances, toxins (including bacterial, viral, fungal and parasitic toxins) as well as antigens and receptors found on pathogens such as bacteria, virus, fungi and parasites are interesting targets/templates for the MIP compositions prepared according to the invention.

Compositions and Pharmaceutical Uses According to the Invention

It is believed that at least some of the MIP compositions obtained by means of the present invention are novel compositions of matter. Hence, the invention also relates to a composition of MIPs having at least one of the following characteristics:

1) the average MIP diameter is less than 20 μm;

2) the average target binding is at least 1 mass unit of target to 10 mass units of MIP;

3) substantially all MIPs in the composition bind the same target molecule, but the composition does not include all binding sites for the target molecule.

It is preferred that 1, 2 or 3 of these characteristics are fulfilled by a composition of the invention, meaning that the composition may have characteristic 1 alone, characteristic 1 and one of characteristics 2 or 2, characteristic 2 alone, characteristic 2 and 3, characteristic 3 alone, or all 3 characteristics 1, 2, and 3.

It is preferred that the average MIP diameter is less than 15 μm, such as less than 10 μm, less than 5 μm, less than 1 μm, less than 900 nm, less than 800 nm, less than 700 nm, less than 600 nm, and even less than 500 nm, 400 nm, 300 nm, and 200 nm.

At any rate, it is preferred that the MIPs in a given composition of the invention do not substantially include particles of more than 50 μm in diameter (such as more than 40, 30, 20, 10, or 1 μm in diameter).

Preferred compositions of the invention bind any one of the target molecules described above, i.e. the "typical examples of useful target molecules" referred to above.

The compositions of the invention (and the compositions prepared according to the methods of the invention) are useful as pharmaceuticals and may be utilised in much the same way as one would utilise antibody compositions. However, due to their stability, the MIP compositions are suitable for oral administration where they, unlike antibodies and many soluble proteinaceous receptors, are stable towards proteolytic degradation in the small intestine. Further, due to the fact that the MIPs may be prepared from materials that are incapable of traversing the gastrointestinal epithelium, they are useful for targeting pathology related molecules/agents which are confined to the gastrointestinal tract. Suitable targets are cholesterol, bile acid and bile acid salts, but also various toxic substances or antigens/ligands found on pathogens in the gastrointestinal tract are possibilities.

However, if the MIPs are prepared from a suitable, biocompatible and/or biodegradable polymer (e.g. Polylactide (PLA), Polyglycolide (PLG)), the may also be employed as parenteral pharmaceuticals, where the danger of raising an undesired immune response against the pharmaceutical agent is reduced when compared to the administration of e.g. antibodies and soluble receptors. In such embodiments, virtually any target molecule which is a suitable target for an antibody or a soluble receptor could be the target for a MIP composition of the invention.

Hence, in a preferred embodiment, the present invention relates to a method for treating, ameliorating or reducing the risk of a disease selected from the group consisting of cardiovascular disease, hypertension, atherosclerosis, heart, gallstone disease, cholestatic liver disease, hypercholesterolemia, obesity, infections originating from parasites, virus or microorganisms e.g. bacteria and fungi, toxification originating from orally received toxins, comprising administering an effective amount of a composition of the invention or a composition prepared according to the invention to a subject in need thereof. This embodiment of the invention also pertains to the use of such compositions in the preparation of a pharmaceutical preparation for the treatment, prophylaxis or amelioration of cardiovascular disease, hypertension, atherosclerosis, gallstone disease, cholestatic liver disease, hypercholesterolemia, obesity, infections originating from parasites, virus or microorganisms such as bacteria and fungi, or toxification originating from orally given toxins. Typically, oral administration is contemplated.

The expected daily dosage of a MIP composition of the invention or prepared according to the invention is at most 40 g per day, but due to the high target capacity of the MIP compositions, smaller daily dosages are contemplated, such as the most 30 g per day, 20 g per day, 10 g per day, 5 g per day, and 1 g per day.

The MIPs may be formulated according to standard methods known to the person skilled in the art, especially formulated for oral use, where it is expected that MIPs will be administered in the form of powders, emulsions, encapsulated emulsions, pills and tablets, but also as ingredients in foodstuffs, where the MIPs can appear disperged in virtually any food or foodstuff.

For formulation of MIPs in such compositions, general reference is made to Mark Gibson, CRC press, 2001, which is hereby incorporated by reference.

Of course, MIP compositions according to the invention and prepared according to the invention may be used in all types of applications where MIPs have been suggested as specific binding partners in the prior art. So, even though the present invention focuses on medical uses of MIP compositions of the invention, this does not exclude the use of the presently disclosed MIP compositions in analytical devices and methods known per se. Hence, the present invention also includes within its scope a method for the quantitative or qualitative determination of a target molecule in a sample, the method comprising contacting the sample with a composition of the invention or prepared according to the invention, wherein MIPs in the composition specifically bind the target molecule, and subsequently performing a quantitative or qualitative assessment of target molecule binding said composition. In this context, the disclosures referred to above, which relate to the general preparation and use of MIPs are all incorporated herein by reference.

PREAMBLE TO THE EXAMPLES

General Method of Making Molecularly Imprinted Polymers

Preparation of MIPs follows the general reaction method of mixing the functional monomer with the print molecule and the cross-linking monomer in a suitable solvent. The choice of monomer is made according to its ability to coordinate the print molecule and is routine for the person skilled in the art. The polymerization is started by adding an initiator in a suitable concentration followed by perturbation with e.g. UV light (for UV initiators) or heat (for heat cleavable initiators).

After polymerization the (often) rigid and crisp polymer is micronized to desired size and the print molecules, unbound monomers and crosslinkers and initiator leftovers are removed by extraction, either by direct wash and/or with the help of refluxing the solvent for a given period of time.

Example 1

MIP with Fluorescein as Template

In a 100 mL flask 1.4 ml of the monomer methacrylic acid (MAA), 9.5 ml ethyleneglycoldimethacrylic acid (EGDMA), 50 mg fluorescein and 10 ml tetrahydrofuran (THF) is mixed on a hot water bath (approx. 40° C.) for 30 min. 2 g of 1,1-azobis(cyclohexane-carbonitrile) (ACHCN) is added slowly. After dissolution the solution is purged with Ar (THF sat'd) for 15 min. The polymerization is initiated by continuous UV light (365 nm, 9W) for 48 hours. The resulting polymer is yellowish crisp and is micronized in a manual mortar to particle sizes between 10 μm and 25 μm. The powder is refluxed in THF for 30 min and washed and filtered several times in ethanol/THF (75:25). The white powder is left to air dry.

Example 2

MIP with Cholic Acid as Template

In a 100 mL flask 1.4 ml of the monomer methacrylic acid (MAA) 9.5 ml ethyleneglycoldimethacrylic acid (EGDMA), 2 g of cholic acid and 12 mL tetrahydrofuran (THF) is mixed on a hot water bath for 30 min. 0.2 g of 2,2'-azobisisobutyronirtile/2,2'-azobis(2-methylpropionitrile) (AIBN) is added slowly. After dissolution the solution is purged with Ar for 15 min. The polymerization is initiated by continuous UV light (365 nm, 9W) for 24 hours on an ice bath. The resulting polymer is yellowish, hard and is micronized in a manual mortar to particle sizes between 25 μm and 50 μm. The powder is refluxed in THF for 30 min (once) and washed and filtered four times in ethanol/THF (75:25). The off-white powder is left to air dry over night.

Example 3

MIP with Cholic Acid as Template

In a 100 ml flask 2.8 ml of the monomer 2-(dimethylamino)-ethylmethacrylic acid (DMA-EMAA) 9.5 ml ethyleneglycoldimethacrylic acid (EGDMA), 2 g of cholic acid and 12 ml tetrahydrofuran (THF) is mixed on a hot water bath for 30 min. 0.8 g of 2,2'-azobisisobutyronirtile/2,2'-azobis(2-methylpropionitrile) (AIBN) is added slowly. After dissolution the solution is purged with Ar for 15 min. The polymerization is initiated by continuous UV light (365 nm, 9W) for 24 hours on an ice bath. The resulting polymer is off-white, crisp and is micronized in a manual mortar to particle sizes between 10 μm and 25 μm. The powder is refluxed twice in THF for 30-60 min and washed and filtered three times in ethanol/THF (75:25). The white powder is left to air dry over night.

Example 4

Binding Capacity of Individual MIP Particles

In order to assess the differences in binding capacity/specificity between the MIP particles in the powder a binding experiment was set up in its simplest form. The MIP's from Example 1 were tested for binding ability towards fluorescein.

1.9 mg of MIP towards fluorescein were suspended in 380 μl ethanol (96%), supplemented with 5 μl of fluorescein solution (0.05 mg/μl in ethanol) and mixed for 5 min. The suspension was centrifuged and the supernatant was removed. The particles were then washed three times with 300 μl of ethanol. The washed particles were spread onto a microscope glass plate and the capacity analysis was done by visually counting the particles in white light (all particles) and the particles showing green fluorescence (binding MIP particles) when exposed to UV light (365 nm). Due to the use of UV light no emission filters were necessary in order to see the green fluorescence.

The pictures shown in FIG. 4 is an overlay picture of the two pictures taken with white light and UV light. The white spots are particles illuminated with white light and the black spots are the UV illuminated green fluorescing particles. From FIG. 4 it is evident that the particles illuminated with white light (white spots) are outnumbering the green fluorescing particles visible when exposed to UV light (black spots). The difference in number of particles visible under the two different light sources demonstrates that the micronization of a MIP results in the provision of a population of binding MIP particles and a population of non-binding MIP particles (=debris); hence a selection of the binding MIP particles based on affinity properties will effectively increase the binding capacity measured as ability to bind the used template per weight unit of MIP employed.

The picture shown is not capable of illustrate our observation that the green fluorescing particles exhibit different degrees (intensity) of green fluorescence not correlated to the particle size. This observation corresponds to differences in binding ability between different binding MIP particles. This intensity (fluorescence) difference again illustrates that the MIP particles do have different binding ability; hence the capacity of the MIP can be increased by selecting the MIP particles with the (in this example) highest fluorescence intensity.

To conclude on this, the present example demonstrates that the binding capacity of a composition of MIP particles can be increased by removing non binding particles. The binding capacity can be further improved by enriching for MIP particles having high affinity and/or multiple exposed binding pockets which bind the target molecule.

LIST OF REFERENCES

1) Yu Cong, Ph.D-thesis: "Molecular Recognition Studies Based on Imprinting Technology", Dept. of Pure and Applied Biochemistry, University of Lund, Sweden 1998.

2) Leif Schweitz, Ph-D-Thesis: "Molecular Imprinted Matrices for Electrochromotography", Technical Analytical Chemistry, University of Lund, Sweden 2001.

3) loana Wärnmark-Surugiu, Ph.D-thesis: "Antibodies and Antibody Mimics in Binding Assays", Dept. of Pure and Applied Biochemistry, University of Lund, Sweden 2002.

4) Dickey F H, "The preparation of specific absorbents" Proc. Natl. Acad. Sci. 35 (1949)227-229.

5) Ramström O et al J. Mol. Recog. 9 (1996)691-696

6) Schweitz L et al J Chromatog. A 792 (1997)401-409

7) Vlatakis G et al "Drug Assay Using Antibody Mimics Made by Molecular Imprinting" Nature 361 (1993)645-647

8) Funke, W. et al Adv. Polym. Sci. 136 (1998) 139-243

9) Van Reis and Zapata U.S. Pat. No. 6,027,650

10) Lihme A et al U.S. Pat. No. 6,620,326

11) Ujam et al Biotechnol Bioeng 83 (2003)554-66, Isolation of monocytes from human peripheral blood . . . )

12) Chase J. Mol. Recognit 11 (1998)217-221

13) Pla et al Biochem. Biophys. Res. Commun. 277 (2000) 381-5

14) Rodgers et al Ann. NY. Acad. Sci. 849 (1998)282-92

15) Hansen CM, "Hansen Solubility Parameters, A Users Handbook CRC Press (ISBN 0-8493-1525-5)

16) Shea K J and Dogherty T K, J. Am. Chem. Soc. 108 (1986)1091-1093

17) Shea K J, Stoddard G J, Shavelle D M, Wakui F and Choate R M Macromolecules 23 (1990)4497-4507

18) Wulff G and Poll H G Makromol. Chem. 188 (1987) 741-748

19) Sellergren, B. et al. (1998), Chem. Mater. 10; 4037-46

20) Whitcombe, M J. et al (1995) J. Am. Chem. Soc. 117; 7105-11

21) Pharmaceutical Preformulation and Formulation: A Practical Guide from Candidate Drug Selection to Commercial Dosage Form, Mark Gibson, CRC press, 2001

22) Kempe and Mosbach (1991), Anal. Lett. 24, 1137-45

23) Ramström et al (1994), Tetrahedron: Asymmetri 5, 649-56

24) Ramström et al (1996 I), J. Mol. Recogn. 9, 691-6

25) Ramström et al (1996 II), Chem. Biol. 3,471-7

26) Liu and Mosbach (1997), Macromol. Rapid. Commun. 18, 609-25

27) Liu and Mosbach (1998), Macromol. Rapid. Commun. 19, 671-4

28) Davidson and Hayes (2002), Current. Org. Chem. 6, 265

29) Andersson et al (1995), Proc. Natl. Acad. Sci. 92, 4788-92

30) Carter (2006), Nat. Rev. Immunol. 6, 343-57

31) Wizeman and Konfinas (2001), Biomat. 22, 1485-91

32) Seong et al (2002), J. Biomater. Sci. Polym. Ed. 13, 637-49

What is claimed is:

1. A method of preparing a composition comprising molecular imprinted polymers having high binding capacity and specificity for a target molecule, said method comprising:

a) obtaining a suspension of insoluble molecular imprinted polymers, which bind the target molecule, and which have been prepared using the target molecule or a mimic thereof as template molecule, b) subjecting the suspended molecular imprinted polymers to an affinity purification procedure, wherein the template molecule or a fragment thereof or a mimic thereof is used as capture agent, c) recovering the molecular imprinted polymers that bind the capture agent in the affinity purification procedure while substantially excluding the capture agent and molecular imprinted polymers that do not bind the capture agent from the recovered product, and d) optionally combining recovered molecular imprinted polymers and a carrier, vehicle or diluent to obtain said composition.

2. The method according to claim 1, wherein the capture agent is coupled covalently or non-covalently to a solid phase.

3. The method according to claim 2, wherein the solid phase is selected from the group consisting of matrices of cross bound carbohydrates, synthetic polymers and combinations thereof.

4. The method according to claim 1, wherein the capture agent consists of or is part of a soluble chemical entity.

5. The method according to claim 4, wherein the capture agent is coupled covalently or non-covalently to a moiety selected from a dendrimer, a substituted carbohydrate, and a substituted soluble polymer in order to expose multiple capture agents per soluble chemical entity.

6. The method according to claim 5 wherein the substituted soluble polymer comprises polyvinyl alcohol and polyethyleneglycol.

7. The method according to claim 1, wherein the capture agent only binds to a fraction of binding sites in the molecular imprinted polymers of step a) that bind the template molecule.

8. The method according to claim 1, wherein the capture agent is a fragment of the template molecule.

9. The method according claim 1, wherein the capture agent comprises the template molecule or mimic thereof or fragment thereof bound to the solid surface or moiety, in a specific orientation so as to substantially avoid exposure to the molecular imprinted polymers of part of the capture agent.

10. The method according to claim 1, wherein the capture agent comprises the template molecule or mimic thereof or fragment thereof bound to the solid surface or moiety, in a non-specific orientation so that substantially all parts of the capture agent are exposed to the molecular imprinted polymers.

11. The method according to claim 1, wherein the affinity purification procedure is selected from the group consisting of expanded bed adsorption (EBA), paramagnetic bead separation, hollow fiber purification, and agglutination.

12. The method according to claim 1, wherein the target molecule is a molecule found in the gastrointestinal tract, such as human gastrointestinal tract.

13. The method according to claim 1, wherein the target molecule is selected from cholesterol, a bile acid, and a bile acid salt.

14. A method of preparing molecular imprinted polymers having high binding capacity for a target molecule, said method comprising:

a) subjecting a raw molecular imprinted polymer, which comprises template molecules consisting of said target molecule or a mimic thereof, to a first step of micronization so as to obtain a molecular imprinted polymer particle size sufficiently small to allow removal of template molecules;

b) removing substantially all template molecules and optionally subjecting the molecular imprinted polymers thus obtained to a second step of micronization, wherein said first and optional second steps of micronization provide for a molecular imprinted polymer average diameter of at most 50 μm; and c) subjecting the molecular imprinted polymers thus obtained to the method according to claim 1.

15. The method according to claim 14, wherein said first and optional second steps of micronization comprise grinding, milling, explosion, hammering, ball milling, cryo grinding, or collision homogenisation.

16. The method according to claim 14, wherein only the first step of micronization is performed.

17. The method according to claim 16, wherein said first step of micronization comprise grinding, milling, explosion, hammering, ball milling, cryo grinding, or collision homogenisation.

18. The method according to claim 14, wherein the target molecule is a molecule found gastrointestinal tract, such as human gastrointestinal tract.

19. The method according to claim 14, wherein the target molecule is pathology related.

20. The method according to claim 14, wherein the target molecule is selected from cholesterol, a bile acid, and a bile acid salt.

21. A composition of insoluble molecular imprinted polymers wherein substantially all molecular imprinted polymers in the composition bind the same target molecule and, optionally, the composition does not include all binding sites for the target molecule.

22. The composition according to claim 21, wherein the insoluble molecular imprinted polymers have an average diameter less than 20 μm.

23. The composition according to claim 21 wherein the average ratio of binding between said molecular imprinted polymers and said target molecule is at least 1 mass unit of target molecule to 10 mass units of molecular imprinted polymer.

24. A composition of insoluble molecular imprinted polymers wherein substantially all molecular imprinted polymers in the composition bind the same target molecule and, optionally, the composition does not include all binding sites for the target molecule, and wherein said composition is prepared according to the method of claim 1.

25. A composition of insoluble molecular imprinted polymers wherein substantially all molecular imprinted polymers in the composition bind the same target molecule and, optionally, the composition does not include all binding sites for the target molecule, and wherein said composition is prepared according to the method of claim 14.

26. The composition according to claim 21, wherein the molecular imprinted polymers in the composition bind cholesterol, bile acid or bile acid salt.

27. The composition according to claim 21 for use as a pharmaceutical.

28. A method for preparing a pharmaceutical for the treatment, prophylaxis or amelioration of cardiovascular disease, hypertension, atherosclerosis, gallstone disease, cholestatic liver disease, hypercholesterolemia, obesity, infections originating from parasites, virus or micro organisms such as bacteria and fungi, or poisoning originating from orally received toxins, said method comprising combining insoluble molecular imprinted polymers wherein substantially all molecular imprinted polymers in the composition bind the same target molecule and, optionally, the composition does not include all binding sites for the target molecule with a pharmaceutically acceptable excipient.

29. The method according to claim 28, wherein the pharmaceutical composition comprises a pharmaceutical excipient acceptable for oral administration.

30. A method for treating, ameliorating or reducing the risk of a disease selected from the group consisting of cardiovascular disease, hypertension, atherosclerosis, gallstone disease, cholestatic liver disease, hypercholesterolemia, obesity, infectious disease caused by a parasite, a virus, a bacteria and a fungi, poisoning originating from orally received toxins, said method comprising administering an effective amount of a composition according to claim 21 to a subject in need thereof.

31. The method according to claim 30, wherein the effective amount is at most 40 g per day.

32. The method according to claim 30, wherein the effective amount is administered orally.

33. A method for the quantitative or qualitative determination of a target molecule in a sample, the method comprising contacting the sample with a composition according to claim 21.

34. A method for the quantitative or qualitative determination of a target molecule in a sample, the method comprising contacting the sample with a composition prepared according to claim 1.

* * * * *

UNITED STATES PATENT AND TRADEMARK OFFICE

CERTIFICATE OF CORRECTION

PATENT NO. : 8,287,908 B2
APPLICATION NO. : 12/279238
DATED : October 16, 2012
INVENTOR(S) : Jesper S. Kristensen et al.

It is certified that error appears in the above-identified patent and that said Letters Patent is hereby corrected as shown below:

Title page (75) Inventors: replace 3rd inventor, first name "Nicholas" with --Nicolas--

Signed and Sealed this
Fourth Day of December, 2012

David J. Kappos
*Director of the United States Patent and Trademark Office*